United States Patent
Qiang et al.

(10) Patent No.: US 11,702,712 B2
(45) Date of Patent: Jul. 18, 2023

(54) CATIONIC CYANURIC CHLORIDE DERIVATIVE TANNING AGENT AND PREPARATION METHOD THEREOF

(71) Applicant: Shaanxi University of Science & Technology, Xi'an (CN)

(72) Inventors: Xihuai Qiang, Xi'an (CN); Xuyang Wang, Xi'an (CN); Chao Xie, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 17/556,206

(22) Filed: Dec. 20, 2021

(65) Prior Publication Data

US 2022/0220569 A1 Jul. 14, 2022

(30) Foreign Application Priority Data

Jan. 9, 2021 (CN) .......................... 202110027187.4

(51) Int. Cl.
*C07D 251/44* (2006.01)
*C14C 3/26* (2006.01)

(52) U.S. Cl.
CPC .............. *C14C 3/26* (2013.01); *C07D 251/44* (2013.01)

(58) Field of Classification Search
CPC .......................... C07D 251/26; C07D 251/44
See application file for complete search history.

(56) References Cited

U.S. PATENT DOCUMENTS 4,402,755 A * 9/1983 Kobayashi ............... C09H 7/00
106/150.1

OTHER PUBLICATIONS

PubChem CID 62869908 (create date: Oct. 22, 2012).*
PubChem CID 428206 (create date: Mar. 26, 2005).*
PubChem CID 62859416 (create date: Oct. 22, 2012).*
PubChem CID 62859419 (create date: Oct. 22, 2012).*

* cited by examiner

*Primary Examiner* — Deepak R Rao
(74) *Attorney, Agent, or Firm* — Hayes Soloway PC

(57) ABSTRACT

A cationic cyanuric chloride derivative tanning agent and a preparation method thereof are disclosed. The method includes: mixing 9.22-36.88 parts of cyanuric chloride, 21.35-100.31 parts of a solvent, and 7.12-33.44 parts of deionized water, all by mass, in an ice-water bath to obtain a mixture A; at a temperature of 0-5° C., adding 2.98-20.44 parts of a tertiary ammonia compound to the mixture A, and subjecting the resulting mixture to a reaction for 4-6 hours, during which its pH value is adjusted with an acid-binding agent solution to 6.0-7.0, to obtain a mixture B; filtering the mixture B, washing the filter cake, and vacuum drying for 4-6 h to obtain a solid C, and grinding to obtain the cationic cyanuric chloride derivative tanning agent.

6 Claims, 6 Drawing Sheets

CATIONIC CYANURIC CHLORIDE DERIVATIVE TANNING AGENT AND PREPARATION METHOD THEREOF

CROSS REFERENCE TO RELATED APPLICATION

This patent application claims the benefit and priority of Chinese Patent Application No. 202110027187.4 filed on Jan. 9, 2021, the disclosure of which is incorporated by reference herein in its entirety as part of the present application.

TECHNICAL FIELD

The present disclosure relates to the technical field of tanning, and in particular to a cationic cyanuric chloride derivative tanning agent and a preparation method thereof.

BACKGROUND ART

A chrome tanning method has always been the most commonly used in the production of different types of light leather in leather industry because of its simplicity and convenience and the achieved good comprehensive tanning performance. However, in the process of chrome tanning, the utilization rate of chrome is only 60%-70%, and the chrome-containing wastewater, sludge and waste chrome shavings produced after tanning have a great impact on the ecological environment. Scholars at home and abroad have done a lot of researches on chrome-free tanning instead of a chrome powder tanning agent, for example replacing a chrome tanning agent with a mineral tanning agent such as titanium and aluminum, or conducting a combined tanning of a vegetable tanning agent with a chrome-free metal salt tanning agent and other organic tanning agents. However, both the zirconium-tanned leather and aluminum-tanned leather are pure white in color and fine and compact in grain surface, but their leather surfaces are relatively hard and not soft enough. The aluminum-tanned leather is not washable and has a low shrinkage temperature. The aldehyde-tanned leather has a fine grain surface, and soft and plump handle, and the most outstanding performance advantage is that it has excellent chemical stability such as sweat resistance, alkali resistance, washing resistance, solvent resistance and oxidation resistance, and good level-dyeing property and color fixative performance, and has a shrinkage temperatures reaching about 80° C. However, there is a risk of formaldehyde generation, and the leather surface of glutaraldehyde-tanned leather is easy to turn yellow. Vegetable-tanned leather is characterized by a plump and compact leather body, a high shrinkage temperature, strong resistances to chemical agents and proteases, and a good hygienic property. However, due to the lack of strong chemical bonding, it is easy to detanning, and defects such as insufficient tanning or a cracked surface may also occur.

In recent years, a cyanuric chloride derivative tanning agent has become the development trend of chrome-free tanning agents in leather making industry. A cyanuric chloride derivative tanning agent (with a trade name Granofin F-90) launched by Stahl for the first time in leather-making enterprises is a novel environmentally-friendly tanning agent, which binds to the amino and carboxyl groups of collagen in a tanning process and releases H$^+$, such that the pH value of a bath solution is automatically reduced, and that the leather-making production process is simplified, and that the production cycle is shortened. In addition, Cui Lu et al. has reported a novel triazine compound as a chrome-free tanning agent, and leather tanned by using this tanning agent has a relatively higher tanning shrinkage temperature and the grain surface of crust leather is white and delicate (Cui L, Qiang X. "Clean Production for Chrome Free Leather by Using a Novel Triazine Compound"[J]. *Journal of Renewable Materials,* 2019). Wu Xiaohui et al. have synthesized a series of cyanuric chloride derivative tanning agents, such as L-Lys/L-Tyr/L-Arg, etc; such tanning agents could be used for tanning without a pickling procedure, the tanned leather has a relatively higher shrinkage temperature, and the grain surface of crust leather is white and delicate (Wu X, et al. "An eco-friendly tanning process to wet-white leather based on amino acids" [J]. *Journal of Cleaner Production,* 2020, 270:122399). However, all of the tannings by using the aforementioned tanning agents would lead to disadvantages such as the strong anionic property of the crust leather and difficulty in dye up-take of anionic dyes.

SUMMARY

An object of the present disclosure is to provide a cationic cyanuric chloride derivative tanning agent and a preparation method thereof, which solve the problems of the strong anionic property of tanned crust leather and difficulty in dye up-take of anionic dyes in the prior art.

The above object of present disclosure is realized by the following technical solutions.

Disclosed is a cationic cyanuric chloride derivative tanning agent, which has a structural formula of

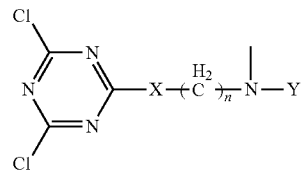

wherein X represents O or NH;
Y represents CH$_3$ or

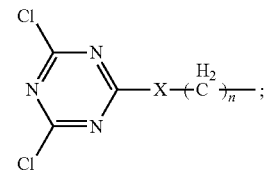

and
n represents 2 or 3.

The present disclosure also discloses a method for preparing the cationic cyanuric chloride derivative tanning agent, including the following steps:

(1) stirring and uniformly mixing 9.22-36.88 parts by mass of cyanuric chloride, 21.35-100.31 parts by mass of a solvent, and 7.12-33.44 parts by mass of deionized water in an ice-water bath, to obtain a mixture A;

(2) at a temperature of 0-5° C., dropwise adding 2.98-20.44 parts of a tertiary ammonia compound to the mixture A, and subjecting the resulting mixture to a reaction for 4-5 hours, during which a pH value of the resulting mixture is adjusted by using an acid-binding agent solution until the pH value is stabilized at 6.0-7.0, to obtain a mixture B; and (3) filtering the mixture B to obtain a filter cake, washing the filter cake, and vacuum drying the washed filter cake under conditions of a vacuum degree of 0.08-0.1 MPa and a temperature of 20-25° C. for 4-6 h to obtain a solid C; grinding and crushing the solid C to obtain the cationic cyanuric chloride derivative tanning agent as a white powder.

In some embodiments, in step (1), the solvent is acetone or toluene.

In some embodiments, in step (2), an acid-binding agent in the acid-binding agent solution is sodium hydroxide or sodium carbonate.

In some embodiments, in step (1), the tertiary ammonia compound is 3-dimethylpropylamine, N-methyldiethanolamine or N,N-bis(3-aminopropyl) methylamine.

In some embodiments, in step (2), the acid-binding agent solution has a mass concentration of 10-30%.

In some embodiments, in step (3), washing the filter cake is performed by using deionized water and/or an acetone solution with a temperature of 0-5° C.

Compared with the prior art, the present disclosure has the following beneficial technical effects.

The present disclosure discloses a cationic cyanuric chloride derivative tanning agent, which has cations, and when used could improve the characteristic that the cationic property of leather fibers tanned by a conventional chrome-free tanning agent is weakened, and meanwhile could improve the absorption and binding of crust leather to anion dyeing and finishing materials in a later dyeing and fat liquoring sections, so that white wet leather and chrome-tanned blue wet leather have good compatibility with dyeing and finishing materials in the subsequent wet-processing. When applied to a tanning procedure of leather making, the cationic cyanuric chloride derivative tanning agent could directly have a better tanning effect on bating bare leather, and a white wet leather with a good performance would be obtained, which avoids a pickling procedure and reduces salt pollution. The cationic chrome-free tanning agent fundamentally eliminates the pollution of chrome tanning agents, other metal tanning agents and aldehyde tanning agents. Also, it is universally applicable in the production procedure of leather making, and does not reduce the cationic property of the fiber surface of the tanned crust leather, which is helpful to improve the adsorption and binding ability of the crust leather to the post-wet dyeing and finishing material.

The present disclosure also discloses a method for preparing the cationic cyanuric chloride derivative tanning agent, which includes the following steps: firstly preparing a cyanuric chloride solution in an ice-water bath, wherein the ice-water bath condition is set to avoid hydrolysis of cyanuric chloride since a second chlorine atom on cyanuric chloride may be reacted under an ambient temperature condition, and meanwhile the hydrolysis of cyanuric chloride is intensified with the increase of temperature in the reaction process. Thereafter, the cyanuric chloride solution is mixed with a tertiary ammonia compound, and the resulting mixture was reacted for a period of time. The pH value of the resulting mixed system is adjusted mainly to promote the synthesis reaction. Finally, the resultant mixture is washed and dried, wherein drying is conducted under a vacuum condition to prevent the product from being hydrolyzed, so as to obtain a product with relatively high purity. The preparation process of the present disclosure is simple and easy to popularize.

Furthermore, a low-temperature washing solution is employed mainly for preventing the hydrolysis of product.

DETAILED DESCRIPTION OF THE EMBODIMENTS

Figure 1:
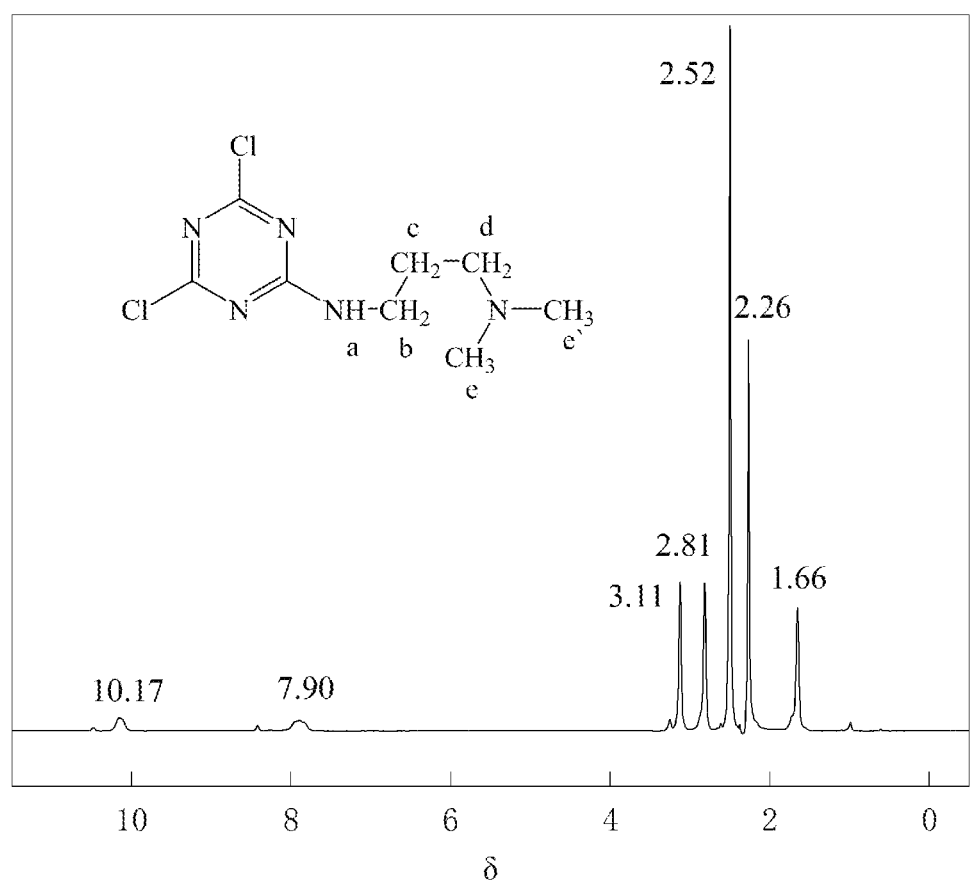
FIG. 1 shows a nuclear magnetic spectrogram of the product as prepared in Example 1.

The present disclosure will be further described in detail below with conjunction with specific examples, which are explanation of the present disclosure rather than limitation.

The present disclosure discloses a method for preparing a cationic cyanuric chloride derivative tanning agent, including the following steps:

(1) stirring and uniformly mixing 9.22-36.88 parts by mass of cyanuric chloride, 21.35-100.31 parts by mass of a solvent, and 7.12-33.44 parts by mass of deionized water in an ice-water bath, to obtain a mixture A;

(2) dropwise adding 2.98-20.44 parts of a tertiary ammonia compound into the mixture A, maintaining a temperature of 0-5° C. and reacting to obtain a mixed system; adjusting a pH of the mixed system by using an acid-binding agent solution until the pH is stabilized at 6.0-7.0, and subjecting the resulting mixture to a reaction for 4-6 hours to obtain a mixture B; and (3) filtering the mixture B to obtain a filter cake, washing the filter cake, and vacuum drying the washed filter cake under conditions of a vacuum degree of 0.08-0.1 MPa and a temperature of 20-25° C. for 4-6 h to obtain a solid C, and grinding and crushing the solid C to obtain the cationic cyanuric chloride derivative tanning agent as a white powder.

The cationic cyanuric chloride derivative tanning agent prepared by the method according to the present disclosure has a structural formula of:

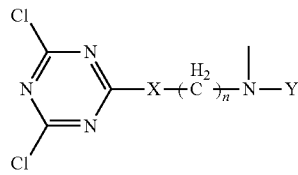

wherein X represents O or NH; n represents 2 or 3; Y represents CH$_3$ or

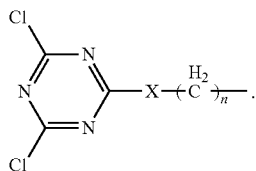

Example 1

The present disclosure discloses a method for preparing a cationic cyanuric chloride derivative tanning agent. One embodiment of the method was performed according to the following procedures:

1) 9.22 g of cyanuric chloride (TCT), 25.08 g of acetone and 8.36 g of deionized water were added into a reactor equipped with a stirrer and a thermometer. The reactor was placed in an ice-water bath, and the resulting mixture therein was uniformly stirred, obtaining a mixture A.

2) At a temperature of 0° C., 5.11 g of 3-dimethylaminopropylamine was slowly dropwise added to the mixture A, and the resulting mixture was then reacted for 4 hours, during which the pH value of the reaction system was continuously adjusted with a sodium carbonate solution having a mass concentration of 10% until the pH value of the reaction system was stabilized at 6.5, obtaining a mixture B.

3) The mixture B was filtered, obtaining a filter cake. The filter cake was washed with deionized water and an acetone solution with a temperature of 3° C. respectively, with a small amount for several times. The washed filter cake was then vacuum-dried under conditions of a vacuum degree of 0.08 MPa and a temperature of 25° C. for 4 h, obtaining a solid C. The solid C was ground and crushed to obtain the cationic cyanuric chloride derivative tanning agent, as a white powder.

The resultant solid was purified, and a pure product was obtained for detection.

Characterization results of the product (i.e. N,N'-2-(4,6-dichloro-1,3,5-triazine-2-amino)-dimethylpropylamine, abbreviated as TAMP) synthesized from TCT and 3-dimethylaminopropylamine are as follows.

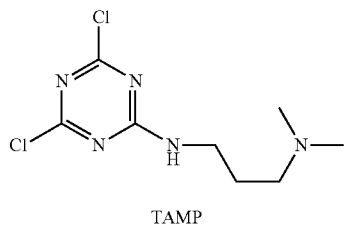

TAMP

Analysis of nuclear magnetic spectrogram is shown in FIG. 1.

Peak at δ 2.52 is a characteristic peak of a testing deuterated reagent (CD$_3$)$_2$SO. Peak at δ 7.90 is assigned to —NH-(a). Peak at δ 3.11 is assigned to —CH$_2$-(b). Peak at δ 2.81 is assigned to —CH$_2$-(d). Peak at δ 1.66 is assigned to —CH$_2$-(c). Peak at δ 2.26 is assigned to —CH$_3$(e, e'). In connection with the aforementioned analysis, it was proved that a target product was successfully prepared.

Figure 2:
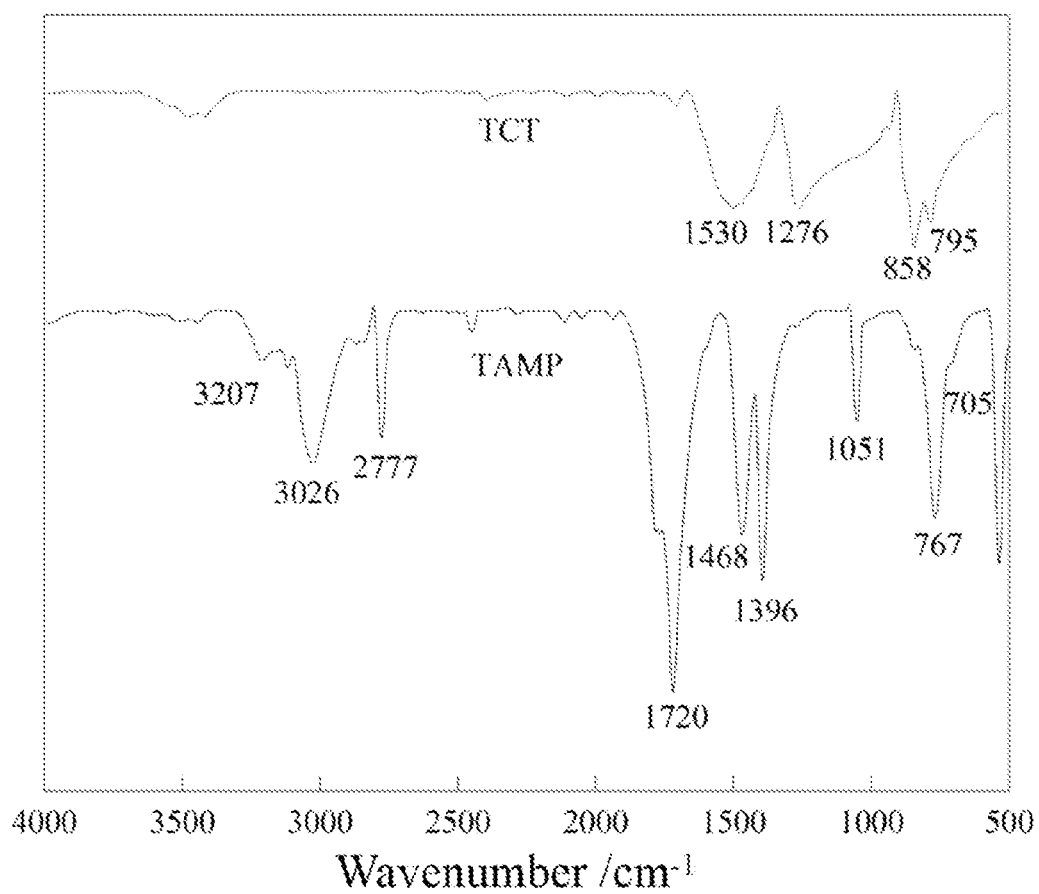
FIG. 2 shows an infrared spectrogram of the product as prepared in Example 1.

Analysis of the infrared spectrogram is shown in FIG. 2.

Peak at 3207 cm$^{-1}$ is ascribed to the stretching vibration of N—H. Peaks at 3026 cm$^{-1}$ and 2777 cm$^{-1}$ are ascribed to the stretching vibration of —CH$_2$—. Peak at 1720 cm$^{-1}$ is ascribed to the stretching vibration of C—N between C and secondary amine in a triazine ring. Peak at 1396 cm$^{-1}$ is ascribed to the stretching vibration of —CH$_3$. Peaks at 1271 cm$^{-1}$ and 1051 cm$^{-1}$ are ascribed to the characteristic absorption of a triazine ring skeleton. Peaks at 848 cm$^{-1}$, 767 cm$^{-1}$, and 705 cm$^{-1}$ are ascribed to the characteristic absorption of C—Cl in a triazine compound, and it could be found that all the three absorption peaks in the TAMP spectrogram has red-shifted when compared with peaks at 1514 cm$^{-1}$ and 1272 cm$^{-1}$ assigned to the triazine ring skeleton in cyanuric chloride and peaks at 885 cm$^{-1}$, 852 cm$^{-1}$, and 796 cm$^{-1}$ assigned to C—Cl characteristic absorption in cyanuric chloride. In connection with the aforementioned analysis, it could be proved that the target product TAMP was successfully prepared.

| Elemental analysis | | |
|---|---|---|
| Element | Theoretical value/% | Test value/% |
| C | 38.40 | 38.79 |
| H | 5.20 | 5.57 |
| Cl | 28.40 | 27.81 |
| N | 28.00 | 27.83 |

It can be seen from the elemental analysis that the measured value of each element in the synthesized compound is basically consistent with the corresponding theoretical value, which indicates that the target product is successfully prepared.

Example 2

The present disclosure discloses a method for preparing a cationic cyanuric chloride derivative tanning agent. One embodiment of the method was performed according to the following procedures:

1) 36.88 g of cyanuric chloride, 100.31 g of toluene, and 33.44 g of deionized water were added into a reactor equipped with a stirrer and a thermometer. The reactor was placed in an ice-water bath, and the resulting mixture was uniformly stirred, obtaining a mixture A.

2) At a temperature of 5° C., 20.44 g of 3-dimethylaminopropylamine was slowly dropwise added to the mixture A, and the resulting mixture was reacted for 4 hours, during which the pH value of the reaction system was continuously adjusted with a sodium hydroxide solution having a mass concentration of 30% until the pH of the system was stabilized at 7.0, obtaining a mixture B.

3) The mixture B was filtered, obtaining a filter cake. The filter cake was washed with deionized water and an acetone solution with a temperature of 0° C. respectively, with a small amount for several times. The washed filter cake was then vacuum dried under conditions of a vacuum degree of 0.1 MPa and a temperature of 22° C. for 6 h, obtaining a solid C. The solid C was ground and crushed, obtaining the cationic cyanuric chloride derivative tanning agent as a white powder.

Example 3

The present disclosure discloses a method for preparing a cationic cyanuric chloride derivative tanning agent. One embodiment of the method was performed according to the following procedures.

1) 9.22 g of cyanuric chloride (TCT), 21.35 g of acetone and 7.12 g of deionized water were added into a reactor equipped with a stirrer and a thermometer. The reactor was placed in an ice-water bath, and the resulting mixture was uniformly stirred, obtaining a mixture A.

2) At a temperature of 1° C., 2.98 g of N-methyldiethanolamine was slowly dropwise added to the mixture A, and the resulting mixture was then reacted for 6 hours, during which the pH value of the reaction system was continuously adjusted with a sodium carbonate solution having a mass concentration of 10% until the pH value of the system was stabilized at 7.0, obtaining a mixture B.

3) The mixture B was filtered, obtaining a filter cake. The filter cake was washed with deionized water and an acetone solution with a temperature of 2° C. respectively, with a small amount for several times. The washed filter cake was then vacuum dried under conditions of a vacuum degree of 0.09 MPa and a temperature of 24° C. for 5 h, obtaining a solid C. The solid C was ground and crushed, obtaining the cationic cyanuric chloride derivative tanning agent as a white powder.

The resultant solid was purified, and a pure product was obtained for detection.

Characterization results of the product (i.e. N,N'-bis-(4,6-dichloro-1,3,5-triazine-2-oxy)-diethylmethylamine, abbreviated as TYDM) synthesized from TCT and N-methyldiethanolamine are as follows.

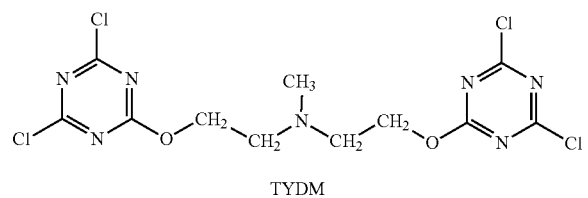

TYDM

Figure 3:
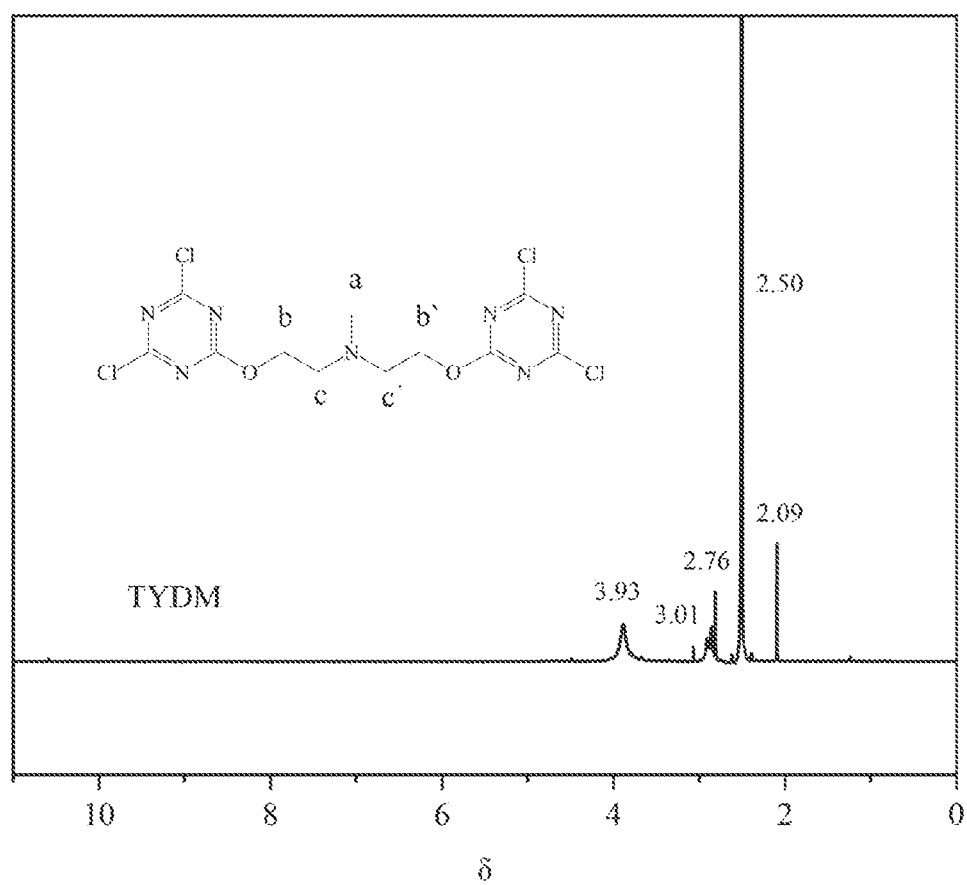
FIG. 3 shows a nuclear magnetic spectrogram of the product as prepared in Example 3.

Analysis of nuclear magnetic spectrogram is shown in FIG. 3.

Peak at δ 2.50 is a characteristic peak of a testing deuterated reagent $(CD_3)_2SO$. Peak at δ 3.93 is assigned to —$CH_2$-(b, b'). Peak at δ 2.76 is assigned to —$CH_2$-(c, c'). Peak at δ 2.09 is assigned to —$CH_3$(a). In view of the above data, the target product was successfully prepared.

Figure 4:
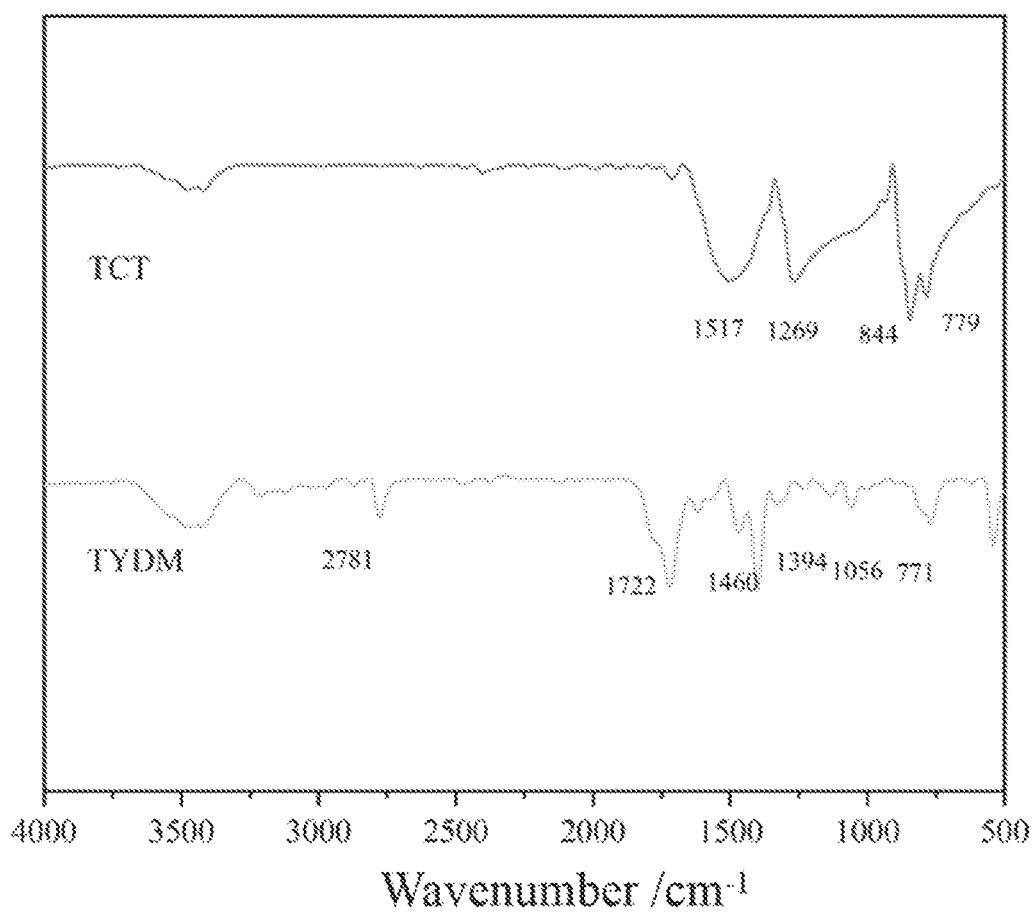
FIG. 4 shows an infrared spectrogram of the product as prepared in Example 3.

Analysis of the infrared spectrogram is shown in FIG. 4.

Peak at 2781 $cm^{-1}$ is ascribed to the stretching vibration of methylene. Peaks at 1460 $cm^{-1}$, 1056 $cm^{-1}$, and 771 $cm^{-1}$ are ascribed to the stretching vibration of a triazine ring skeleton, which have red-shifted compared with the stretching vibration peaks of the triazine ring skeleton in cyanuric chloride. Peak at 1394 $cm^{-1}$ is ascribed to the stretching vibration of an ether bond. In view of the above, the target product was successfully prepared.

| Elemental analysis | | |
|---|---|---|
| Element | Theoretical value/% | Test value/% |
| C | 31.81 | 31.22 |
| H | 2.65 | 2.95 |
| O | 7.71 | 8.51 |
| Cl | 34.22 | 33.90 |
| N | 23.61 | 23.42 |

It can be seen from the elemental analysis that, the measured value of each element in the synthesized compound is basically consistent with the corresponding theoretical value, which indicates that the target product is successfully prepared.

Example 4

The present disclosure discloses a method for preparing a cationic cyanuric chloride derivative tanning agent. One embodiment of the method was performed according to the following procedures.

1) 36.88 g of cyanuric chloride, 85.40 g of toluene and 28.47 g of deionized water were added into a reactor equipped with a stirrer and a thermometer. The reactor was placed in an ice-water bath, and the resulting mixture was uniformly stirred, obtaining a mixture A.

2) At a temperature of 5° C., 11.92 g of N-methyldiethanolamine was slowly dropwise added to the mixture A, and the resulting mixture was then reacted for 6 hours, during which the pH value of the reaction system was continuously adjusted with a sodium hydroxide solution having a mass concentration of 30% until the pH value of the reaction system was stabilized at 6.0, obtaining a mixture B.

3) The mixture B was filtered, obtaining a filter cake. The filter cake was washed with deionized water and an acetone solution with a temperature of 4° C. respectively, with a small amount for several times. The washed filter cake was then vacuum dried under conditions of a vacuum degree of 0.1 MPa and a temperature of 22° C. for 5 h, obtaining a solid C. The solid C was ground and crushed, obtaining the cationic cyanuric chloride derivative tanning agent as a white powder.

Example 5

The present disclosure discloses a method for preparing a cationic cyanuric chloride derivative tanning agent. One embodiment of the method was performed according to the following procedures.

1) 18.44 g of cyanuric chloride (TCT), 45.00 g of acetone, and 15.00 g of deionized water were added into a reactor equipped with a stirrer and a thermometer. The reactor was placed in an ice-water bath, and the resulting mixture was uniformly stirred, obtaining a mixture A.

2) At a temperature of 5° C., 7.27 g of N,N-bis(3-aminopropyl)methylamine was slowly dropwise added to the mixture A, and the resulting mixture was then reacted for 5 hours, during which the pH value of the mixed system was continuously adjusted with a sodium hydroxide solution having a mass concentration of 30% until the pH value of the resulting system was stabilized at 6.0, obtaining a mixture B.

3) The mixture B was filtered, obtaining a filter cake. The filter cake was washed with deionized water and an acetone solution with a temperature of 4° C. respectively, with a small amount for several times. The washed filter cake was then vacuum dried under conditions of a vacuum degree of 0.1 MPa and a temperature of 20° C. for 5 h, obtaining a solid C. The solid C was ground and crushed, obtaining the cationic cyanuric chloride derivative tanning agent as a white powder.

The resultant solid was purified, and a pure product was obtained for detection.

Characterization results of the product (i.e. N,N'-bis-(4,6-dichloro-1,3,5-triazine-2-amino)-dipropylmethylamine, abbreviated as TADM) synthesized from TCT and N,N-bis (3-aminopropyl)methylamine are as follows.

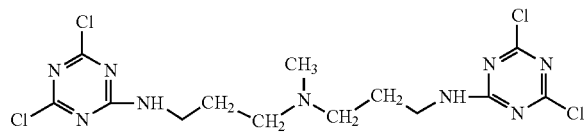 [SMILES: CN(CCCNc1nc(Cl)nc(Cl)n1)CCCNc1nc(Cl)nc(Cl)n1]

Figure 5:
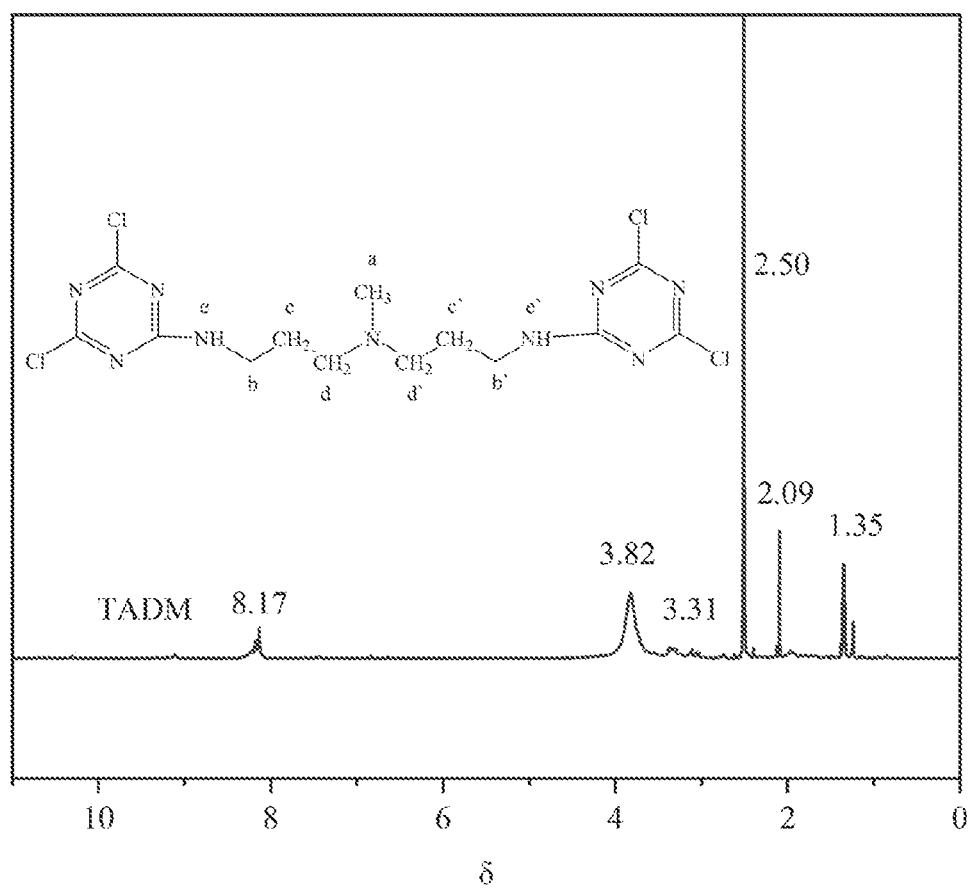
FIG. 5 shows a nuclear magnetic spectrogram of the product as prepared in Example 5.

Analysis of nuclear magnetic spectrogram is shown in FIG. 5.

Peak at δ 2.50 is the characteristic peak of a testing deuterated reagent $(CD_3)_2SO$. Peak at δ 8.17 is assigned to —NH-(e, e'). Peaks at δ 3.82 and δ 1.35 are assigned to —$CH_2$-(c, c'). Peak at δ 3.31 is assigned to —$CH_2$-(b, b'). Peak at δ 3.31 is assigned to —$CH_2$-(d, d'). And peak at δ 2.09 is assigned to —$CH_3$(a). In view of the above, the target product was successfully prepared.

Figure 6:
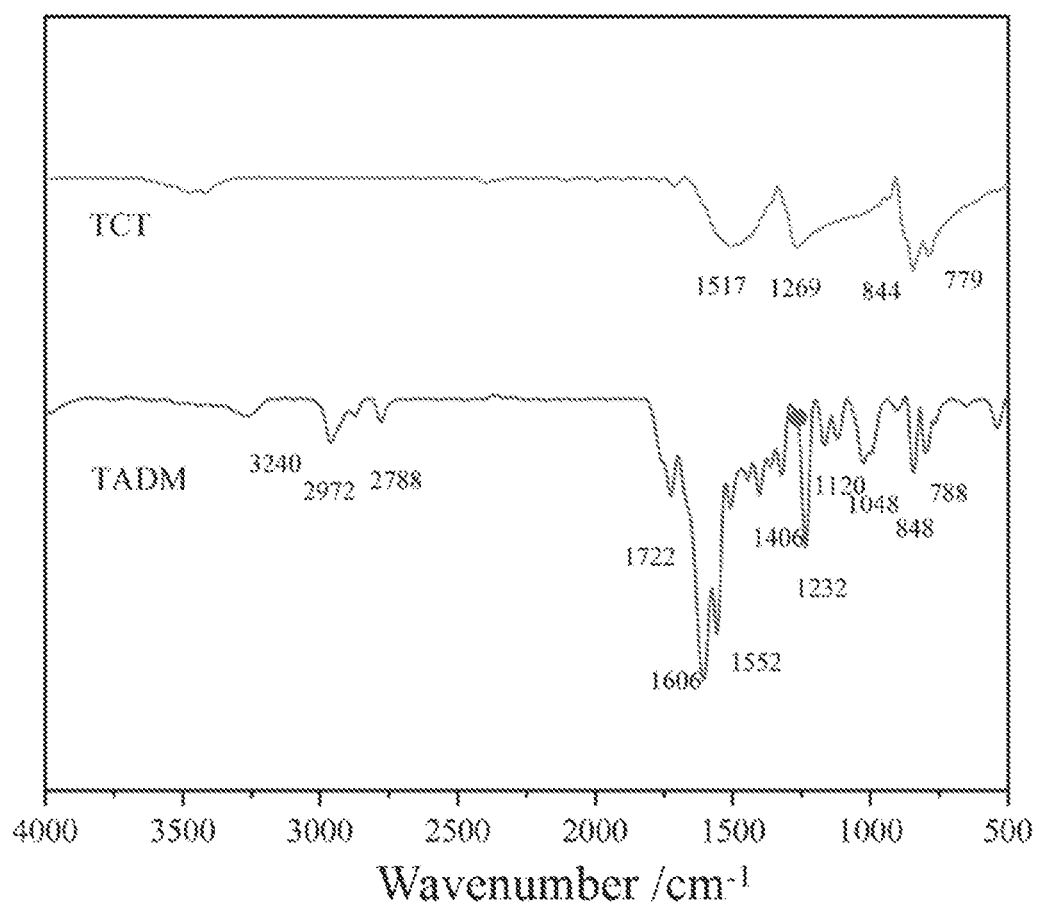
FIG. 6 shows an infrared spectrogram of the product as prepared in Example 5.

Analysis of the infrared spectrogram is shown in FIG. 6.

Peak at 3240 $cm^{-1}$ is ascribed to the stretching vibration of N—H. Peaks at 2972 $cm^{-1}$ and 2788 $cm^{-1}$ are ascribed to the stretching vibration of —$CH_2$—. Peak at 1722 $cm^{-1}$ is ascribed to the stretching vibration of C—N between C and secondary amine in a triazine ring. Peak at 1406 $cm^{-1}$ is ascribed to the stretching vibration of —$CH_3$. Peaks at 1232 $cm^1$ and 1048 $cm^{-1}$ are ascribed to the characteristic absorption of a triazine ring skeleton, which has red-shifted compared with the peaks at 1514 $cm^{-1}$ and 1272 $cm^{-1}$ assigned to the triazine ring skeleton in cyanuric chloride. In connection with the aforementioned analysis, it could be proved that the target product TAMP was successfully prepared.

| Elemental analysis | | |
|---|---|---|
| Element | Theoretical value/% | Test value/% |
| C | 35.37 | 36.22 |
| H | 3.86 | 4.37 |
| Cl | 32.20 | 31.50 |
| N | 28.57 | 27.91 |

It can be seen from the elemental analysis that the measured value of each element in the synthesized compound is basically consistent with the corresponding theoretical value, which indicates that the target product is successfully prepared.

Example 6

The present disclosure discloses a method for preparing a cationic cyanuric chloride derivative tanning agent. One embodiment of the method was performed according to the following procedures.

1) 36.88 g of cyanuric chloride, 90.00 g of toluene and 30.00 g of deionized water were added into a reactor equipped with a stirrer and a thermometer. The reactor was placed in an ice-water bath, and the resulting mixture was uniformly stirred, obtaining a mixture A.

2) At a temperature of 4° C., 14.53 g of N,N-bis(3-aminopropyl)methylamine was slowly dropwise added to the mixture A, and the resulting mixture was then reacted for 5 hours, during which the pH value of the reaction system was continuously adjusted with a sodium carbonate solution having a mass concentration of 10% until the pH value of the reaction system was stabilized at 7.0, obtaining a mixture B.

3) The mixture B was filtered, obtaining a filter cake. The filter cake was washed with deionized water and an acetone solution with a temperature of 1° C. respectively, with a small amount for several times. The washed filter cake was then vacuum dried under conditions of a vacuum degree of 0.08 MPa and a temperature of 23° C. for 6 h, obtaining a solid C. The solid C was ground and crushed, obtaining the cationic cyanuric chloride derivative tanning agent as a white powder.

Use of the Products of Examples

Salted sheep leather was subjected to a conventional processes: pre-soaking in water→main soaking in water-→degreasing→lime-sulfide unhairing→weighing→liming→fleshing→weighing→deliming→bating→washing with water (the dosages of materials for the tanning experiment were calculated in terms of the weight of the limed skin; the specific tanning experiment process is shown in Table 1). The shrinkage temperature, sensory state of the white wet leather obtained after tanning, the observation results of the tanning waste fluid state are shown in Table 2. After the tanned crust leather was placed and aged for two or three days, such that the moisture content of the crust leather was maintained between 40 and 50%. The crust leather was then weighed and subjected to dyeing treatment according to the process shown in Table 3, and compared with the crust leather tanned with F-90. The dye absorption rate during dyeing and the observation results of dyeing effect are shown in Table 4.

TABLE 1

| | Tanning process | | | | |
|---|---|---|---|---|---|
| Operation | Material | Dosage/% | Temperature/° C. | Time/min | Remarks |
| Tanning | water | 200 | 25 | | |
| | Sodium chloride | 10 | | | |
| | Products of Examples | 4 | | 120 | |
| Leather basifying | Sodium Bicarbonate | 1.5 | 45 | 120 | Adding for 4 times, pH = 6.0-6.5 |
| | Sodium Carbonate | 1.0 | 45 | 120 | Adding for 2 times, pH = 7.0-7.5 | the drum running was stopped, and it was left to stand overnight, and rotated for 30 min on the next day, then the leather was stacked and allowed to stand, and the waste fluid was collected

TABLE 2

Observation results of tanning waste fluid and shrinkage temperature of the white wet leather

| Chromium-free tanning agent | Shrinkage temperature/ °C. | Sensory state of crust leather | Color of waste fluid |
|---|---|---|---|
| Example 1 | 73 | White and delicate | Clear |
| Example 2 | 72 | White and delicate | Clear |
| Example 3 | 75 | White and delicate | Milky white clear solution |
| Example 4 | 76 | White and delicate | Milky white clear solution |
| Example 5 | 76 | White and delicate | Relatively clear |
| Example 6 | 75 | White and delicate | Relatively clear |

TABLE 3

Tanning and dyeing processes

| Operation | Material | Dosage/ % | Temperature/ °C. | Time/ min | Remarks |
|---|---|---|---|---|---|
| Washing with water | water | 200 | 25 | 30 | Draining |
| Neutralizing | water | 150 | | | |
| | Sodium bicarbonate | 0.5 | | | |
| | Sodium acetate | 1.5 | 35 | 60 | pH = 6.5, draining |
| Washing with water | water | 200 | 25 | 30 | pH = 6.5, draining |
| Dyeing and fat liquoring | water | 150 | | | |
| | Direct Red 23 | 3 | | | |
| | Synthetic fat liquoring agent | 10 | 50 | 60 | |
| Color fixation | Formic acid | 1.0 | 40 | 60 | pH = 3.5-4.0, draining |

The waste fluid was collected, and the leather was stacked, allowed to stand and dried

TABLE 4

Observation results of dyeing waste fluid and comparison with F-90 dyeing

| Dyed crust leather | Color of waste fluid | Dye absorptivity |
|---|---|---|
| Example 1 | Red and clear | 92 |
| Example 2 | Red and clear | 93 |
| Example 3 | Red and clear | 93 |
| Example 4 | Red and clear | 95 |
| Example 5 | Red and clear | 94 |
| Example 6 | Red and clear | 95 |
| F-90 | Red and relatively clear | 84 |

It can be seen from Table 2 that the cationic compound of the present disclosure, which has a core of cyanuric chloride, when used as a chrome-free tanning agent for the tanning of white wet leather, has advantage of good absorption, allows for white, flat and fine grain surface of tanned crust leather. By analysis in connection with Table 4, it can be seen that the crust leather prepared by using such tanning agent is easy to dye and has a good dyeing performance, which could provide a chrome-free tanning agent with a good performance and a feasible application process technology for the leather making industry to realize chrome-free tanning

What is claimed is:

1. A cationic cyanuric chloride derivative tanning agent, which has a structural formula of

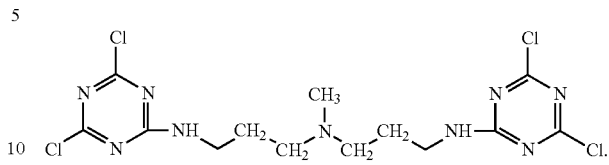

2. A method for preparing the cationic cyanuric chloride derivative tanning agent as claimed in claim 1, comprising
(1) mixing 9.22-36.88 parts by mass of cyanuric chloride, 21.35-100.31 parts by mass of a solvent, and 7.12-33.44 parts by mass of deionized water in an ice-water bath, to obtain a mixture A;
(2) at a temperature of 0-5° C., dropwise adding 2.98-20.44 parts of N,N-bis(3-aminopropyl)methylamine into the mixture A, and subjecting the resulting mixture to a reaction for 4-6 hours, during which a pH value of the resulting mixture is adjusted by using an acid-binding agent solution until the pH value is stabilized at 6.0-7.0, to obtain a mixture B; and
(3) filtering the mixture B to obtain a filter cake, washing the filter cake, vacuum drying the washed filter cake under conditions of a vacuum degree of 0.08-0.1 MPa and a temperature of 20-25° C. for 4-6 h to obtain a solid C; grinding and crushing the solid C to obtain the cationic cyanuric chloride derivative tanning agent as a white powder.

3. The method as claimed in claim 2, wherein in step (1), the solvent is acetone or toluene.

4. The method as claimed in claim 2, wherein in step (2), an acid-binding agent in the acid-binding agent solution is sodium hydroxide or sodium carbonate.

5. The method as claimed in claim 2, wherein in step (2), the acid-binding agent solution has a mass concentration of 10-30%.

6. The method as claimed in claim 2, wherein in step (3), washing the filter cake is performed by using deionized water and/or an acetone solution with a temperature of 0-5° C.

* * * * *